United States Patent
Shim et al.

(10) Patent No.: US 10,768,285 B2
(45) Date of Patent: Sep. 8, 2020

(54) METHOD AND APPARATUS FOR OBTAINING ELASTIC FEATURE OF OBJECT

(71) Applicant: SAMSUNG ELECTRONICS CO., LTD., Suwon-si (KR)

(72) Inventors: Hwan Shim, Yongin-si (KR); Young-tae Kim, Seongnam-si (KR); Hyung-joon Lim, Seoul (KR); Yun-sub Jung, Yongin-si (KR); Byeong-geun Cheon, Anyang-si (KR); Min-Gu Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1235 days.

(21) Appl. No.: 14/913,715

(22) PCT Filed: Oct. 6, 2014

(86) PCT No.: PCT/KR2014/009371
§ 371 (c)(1),
(2) Date: Feb. 23, 2016

(87) PCT Pub. No.: WO2015/053515
PCT Pub. Date: Apr. 16, 2015

(65) Prior Publication Data
US 2016/0199035 A1 Jul. 14, 2016

(30) Foreign Application Priority Data
Oct. 7, 2013 (KR) .......................... 10-2013-0119457

(51) Int. Cl.
*G01S 7/52* (2006.01)
*A61B 8/08* (2006.01)

(52) U.S. Cl.
CPC ........ *G01S 7/52042* (2013.01); *A61B 8/5215* (2013.01); *G01S 7/52022* (2013.01); *A61B 8/485* (2013.01)

(58) Field of Classification Search
None
See application file for complete search history.

(56) References Cited

U.S. PATENT DOCUMENTS 5,810,731 A * 9/1998 Sarvazyan ............... A61B 8/08
600/438
6,023,977 A * 2/2000 Langdon ................ G01N 29/06
367/87

(Continued)

FOREIGN PATENT DOCUMENTS

| CN | 102018533 A | 4/2011 |
|----|-------------|--------|
| CN | 103096812 A | 5/2013 |

(Continued)

OTHER PUBLICATIONS

Communication dated Jun. 27, 2017, issued by the Japanese Patent Office in counterpart Japanese Application No. 2016-538870.

(Continued)

*Primary Examiner* — Katherine L Fernandez
(74) *Attorney, Agent, or Firm* — Sughrue Mion, PLLC

(57) ABSTRACT

A method for obtaining an elastic feature of an object includes inducing a first shear wave in the object by transmitting a first push ultrasound signal which is generated by a probe of an ultrasound apparatus and a first grating lobe signal which relates to the first push ultrasound signal toward the object, transmitting a tracking ultrasound signal to an area of the object where the first shear wave has propagated, receiving, from the object, a reflection signal which relates to the tracking ultrasound signal, measuring a first shear wave parameter which indicates a shear wave characteristic of the first shear wave based on the reflection (Continued)

signal, and obtaining an elastic feature of the object by using the first shear wave parameter.

13 Claims, 4 Drawing Sheets

(56) References Cited

U.S. PATENT DOCUMENTS

| | | | |
|---|---|---|---|
| 7,252,004 B2 | 8/2007 | Fink et al. | |
| 8,500,639 B2 | 8/2013 | Yao | |
| 8,801,614 B2 | 8/2014 | Hsu et al. | |
| 9,351,707 B2 | 5/2016 | Tamura | |
| 2005/0101865 A1 | 5/2005 | Hao et al. | |
| 2005/0183505 A1 | 8/2005 | Kono et al. | |
| 2005/0277853 A1* | 12/2005 | Mast | A61N 7/022 601/2 |
| 2010/0317971 A1* | 12/2010 | Fan | A61B 8/08 600/439 |
| 2011/0066030 A1 | 3/2011 | Yao | |
| 2011/0263978 A1* | 10/2011 | Chen | A61B 8/48 600/438 |
| 2012/0296215 A1 | 11/2012 | Brown et al. | |
| 2013/0211253 A1 | 8/2013 | Hsu et al. | |
| 2014/0046173 A1* | 2/2014 | Greenleaf | G01N 21/17 600/411 |

FOREIGN PATENT DOCUMENTS

| | | |
|---|---|---|
| CN | 103239258 A | 8/2013 |
| JP | 2002-65670 A | 3/2002 |
| KR | 10-2002-0089403 A | 11/2002 |
| WO | 2012085812 A2 | 6/2012 |
| WO | 2012/116364 A1 | 8/2012 |

OTHER PUBLICATIONS

Chen, et al., "Quantifying elasticity and viscosity from measurement of shear wave speed dispersion", Acoustical Society of America, vol. 115, No. 6, Jun. 2004, pp. 2781-2785.
International Search Report for PCT/KR2014/009371 dated Jan. 12, 2015 [PCT/ISA/210].
Written Opinion for PCT/KR2014/009371 dated Jan. 12, 2015 [PCT/ISA/237].
Communication dated Jan. 20, 2017, from the European Patent Office in counterpart European Application No. 14852061.2.
Communication dated Dec. 13, 2016, from the Japanese Patent Office in counterpart application No. 2016-538870.
Communication dated May 4, 2018, from the State Intellectual Property Office of People's Republic of China in counterpart Application No. 201480055440.5.

* cited by examiner

[Fig. 1]
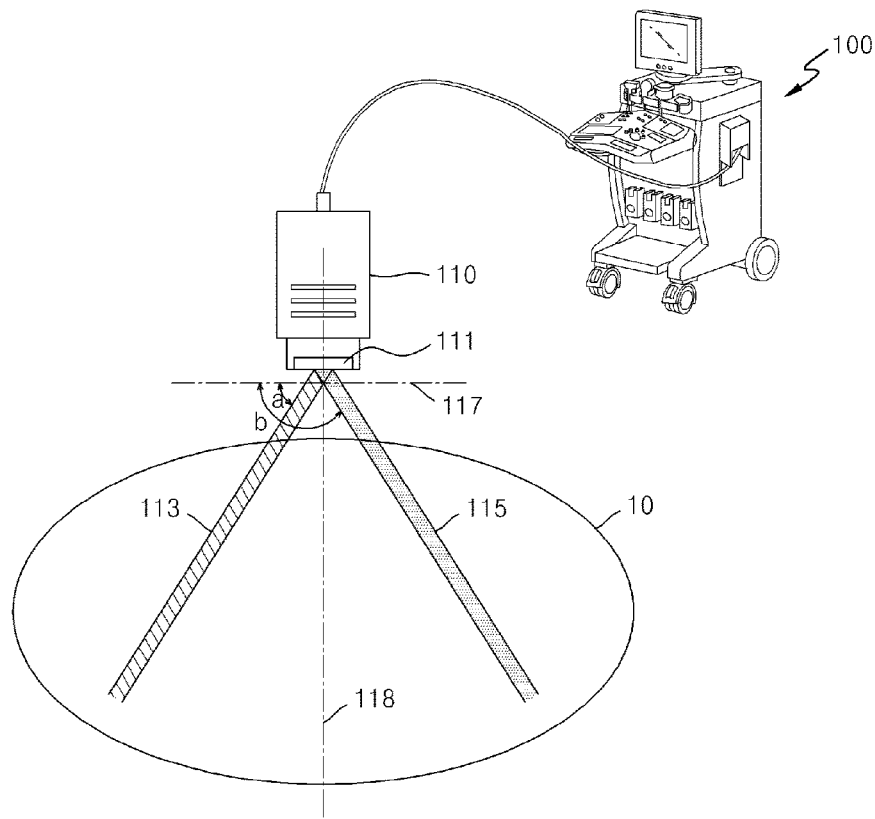
[Fig. 2]
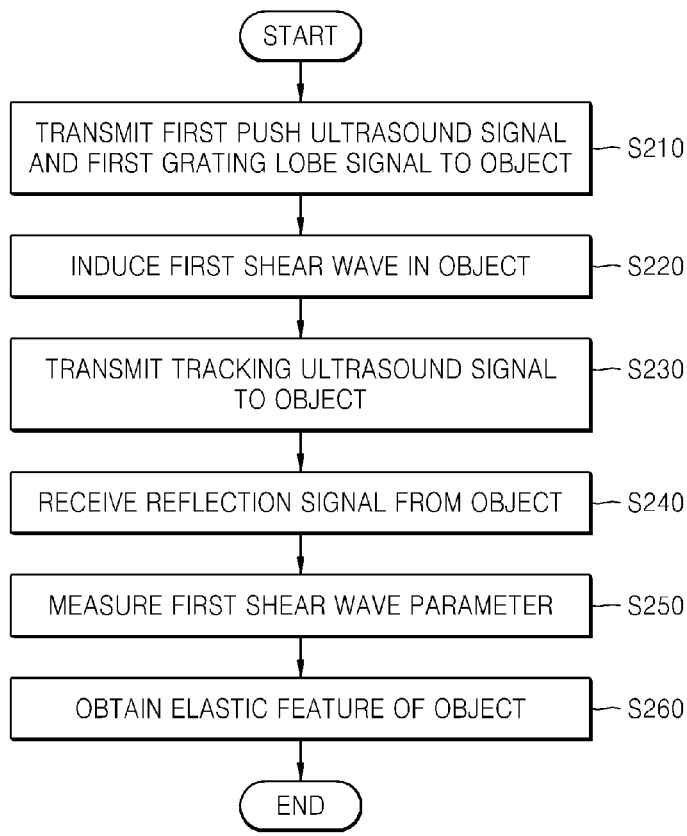

[Fig. 3]
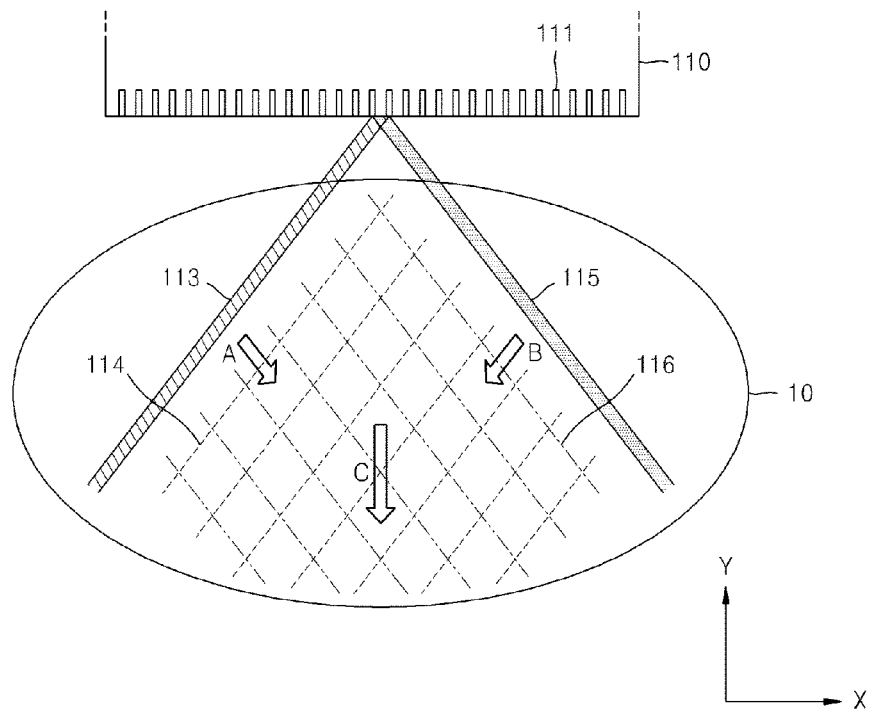
[Fig. 4]
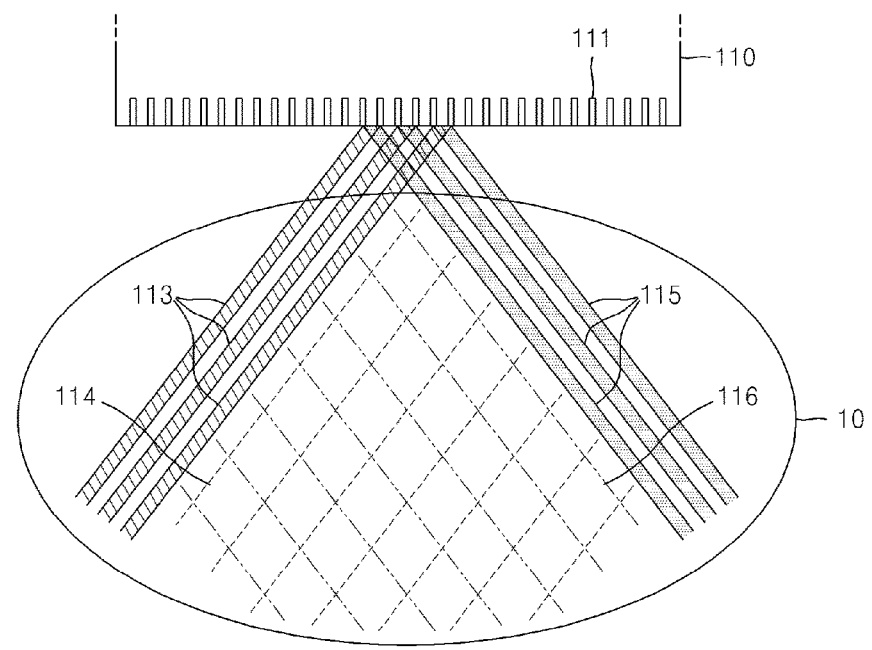

[Fig. 5]
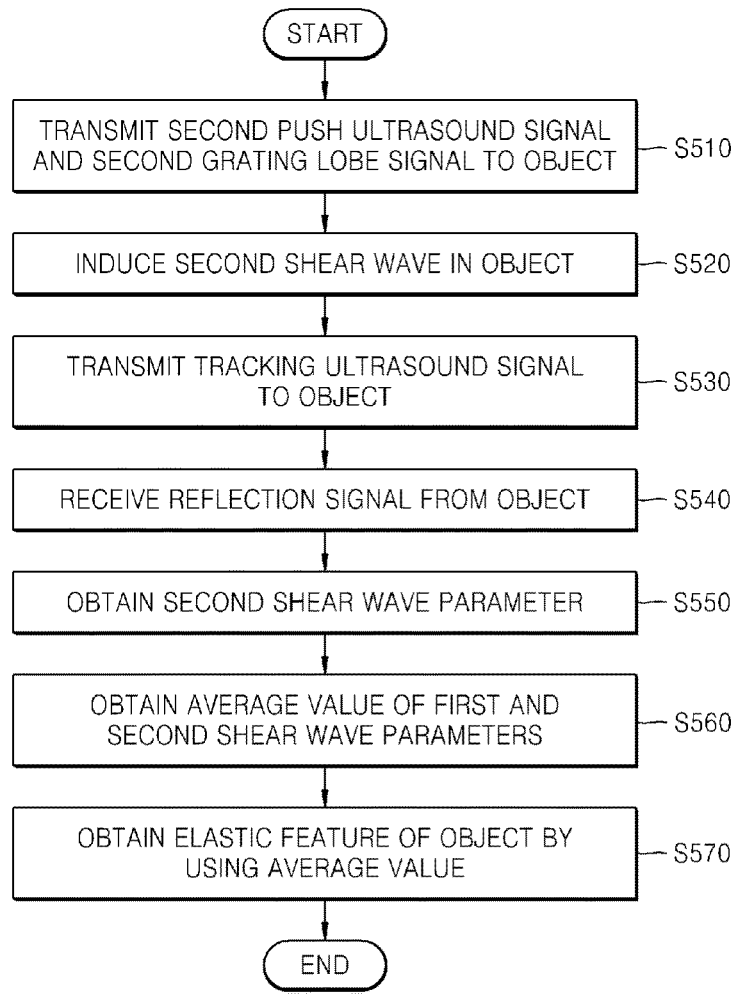
[Fig. 6]
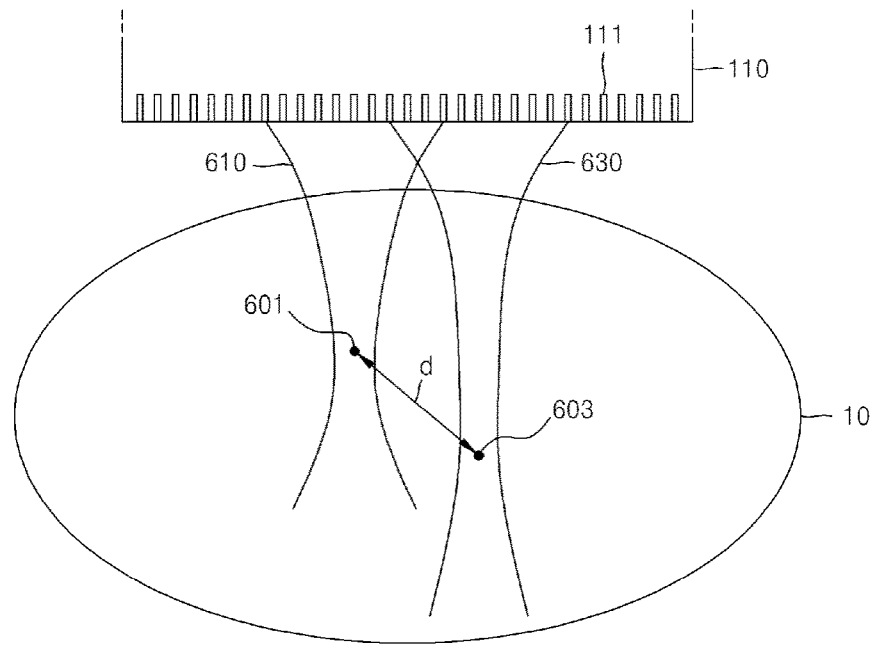

[Fig. 7]
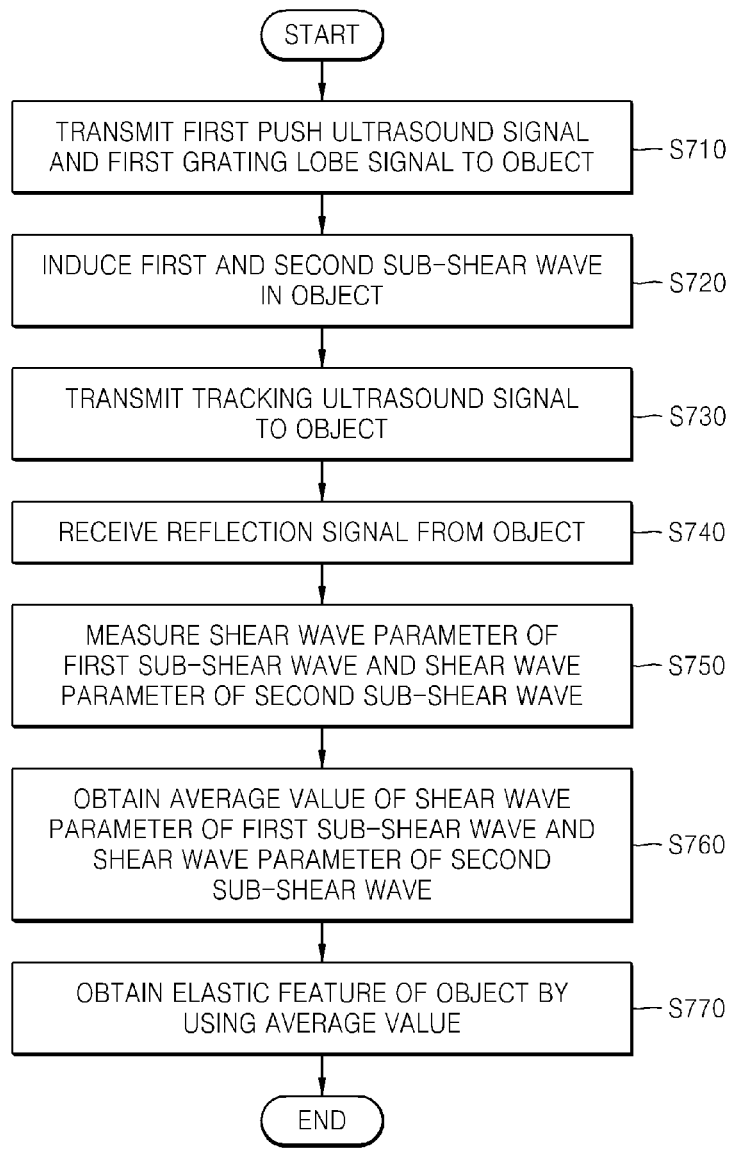
[Fig. 8]
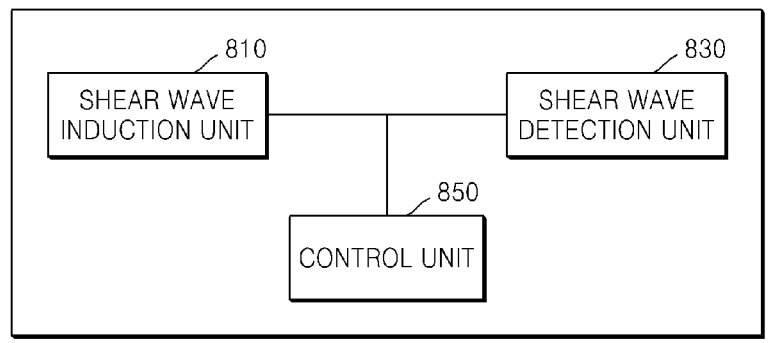

METHOD AND APPARATUS FOR OBTAINING ELASTIC FEATURE OF OBJECT

TECHNICAL FIELD

One or more exemplary embodiments relate to a medical diagnosis field, and more particularly, to a method and apparatus for obtaining an elastic feature of an object by using an ultrasound apparatus.

BACKGROUND ART

A general ultrasound apparatus is a non-invasive test apparatus and is used to show structural details, internal tissues, and the flow of liquids in a body. An ultrasound apparatus transmits an ultrasound signal to an object and generates an ultrasound image of the object by using a response signal reflected from the object. The ultrasound image is mainly presented as a B mode image which is generated as a function of a reflection coefficient which varies based on a difference in impedance between tissues. However, an object such as a malignant tumor, for which the variation in the reflection coefficient may be relatively small as compared to surrounding tissues, is difficult to observe in the B mode image.

In particular, it is often difficult to discern, in the B mode image, a difference in dispersion efficiency between a normal tissue and an abnormal tissue. Accordingly, methods of distinguishing a normal tissue and an abnormal tissue by obtaining an elastic feature of a medium when an external pressure is applied or not applied to the medium have been suggested.

U.S. Pat. No. 5,810,731 discloses a method of obtaining an elastic feature of an object by transmitting a focused ultrasound signal to an object to induce shear waves in the object and measuring a shear wave feature.

However, in the disclosed methods, shear waves are not induced in an area which is perpendicular to a position of the object where a user locates a probe, that is, an area where a focused ultrasound signal is propagated, because the focused ultrasound signal is transmitted to the object in a direction which is perpendicular to the probe in order to induce shear waves in a direction which is perpendicular to the direction in which the focused ultrasound signal is propagated. In this aspect, even when a user locates a probe near an object in order to measure an elastic feature of a partial area of the object, according to a method of the related art, an elastic feature of a part of the object which is located under the position where the probe is located may not be obtained.

Further, according to the methods of the related art, since the shear waves are induced in the object by using the focused ultrasound signal, there may be an increased risk due to a high sound pressure of the focused ultrasound signal.

DISCLOSURE OF INVENTION

Technical Problem

One or more exemplary embodiments include an apparatus and method for accurately and quickly obtaining an elastic feature of an object.

Solution to Problem

According to one or more exemplary embodiments, a method for obtaining an elastic feature of an object includes inducing a first shear wave in the object by transmitting a first push ultrasound signal which is generated by a probe of an ultrasound apparatus and a first grating lobe signal which relates to the first push ultrasound signal toward the object, transmitting a first tracking ultrasound signal to an area of the object where the first shear wave has propagated, and receiving, from the object, a first reflection signal which relates to the first tracking ultrasound signal, measuring a first shear wave parameter which indicates a shear wave characteristic of the first shear wave based on the first reflection signal, and obtaining an elastic feature of the object by using the measured first shear wave parameter.

BRIEF DESCRIPTION OF DRAWINGS

FIG. 1 illustrates an ultrasound apparatus which is configured for transmitting a first push ultrasound signal and a first grating lobe signal to an object, according to an exemplary embodiment;

FIG. 2 is a flowchart which illustrates a method for obtaining an elastic feature of an object, according to an exemplary embodiment;

FIG. 3 illustrates an exemplary method by which an ultrasound apparatus induces a first shear wave in the object, according to an exemplary embodiment;

FIG. 4 illustrates an exemplary method by which an ultrasound apparatus induces a first shear wave in the object, according to another exemplary embodiment;

FIG. 5 is a flowchart which illustrates a method for obtaining an elastic feature of an object, according to another exemplary embodiment;

FIG. 6 illustrates a method by which the ultrasound apparatus measures a propagation velocity of the first shear wave, according to an exemplary embodiment;

FIG. 7 is a flowchart which illustrates a method for obtaining an elastic feature of an object, according to another exemplary embodiment; and FIG. 8 is a block diagram which illustrates a structure of an ultrasound apparatus, according to an exemplary embodiment.

BEST MODE FOR CARRYING OUT THE INVENTION

According to one or more exemplary embodiments, a method for obtaining an elastic feature of an object includes inducing a first shear wave in the object by transmitting a first push ultrasound signal which is generated by a probe of an ultrasound apparatus and a first grating lobe signal which relates to the first push ultrasound signal toward the object, transmitting a first tracking ultrasound signal to an area of the object where the first shear wave has propagated, and receiving, from the object, a first reflection signal which relates to the first tracking ultrasound signal, measuring a first shear wave parameter which indicates a shear wave characteristic of the first shear wave based on the first reflection signal, and obtaining an elastic feature of the object by using the measured first shear wave parameter.

The first push ultrasound signal may include an unfocused ultrasound signal.

In the inducing of the first shear wave, the first shear wave may be induced in the object by transmitting a plurality of first push ultrasound signals and a plurality of first grating lobe signals which respectively relate to the first push ultrasound signals, both pluralities having a same steering angle, toward the object by using a plurality of elements which are included in the probe.

The inducing the first shear wave may include transmitting the first push ultrasound signal toward the object by steering the first push ultrasound signal at a first steering angle.

The method may further include inducing a second shear wave in the object by transmitting a second push ultrasound signal which is steered at a second steering angle that is different from the first steering angle and a second grating lobe signal which relates to the second push ultrasound signal toward the object, transmitting a second tracking ultrasound signal to an area of the object where the second shear wave has propagated and receiving, from the object, a second reflection signal which relates to the second tracking ultrasound signal, and measuring a second shear wave parameter which indicates a shear wave characteristic of the second shear wave based on the second reflection signal. In the above method, the obtaining of the elastic feature of the object comprises using the measured first shear wave parameter and the measured second shear wave parameter to determine an average parameter value and obtaining the elastic feature of the object by using the determined average parameter value.

The receiving the first reflection signal may include transmitting the first tracking ultrasound signal a plurality of times to an area where the first shear wave has propagated and receiving, from the object, a plurality of first reflection signals which relate to the plurality of transmissions of the first tracking ultrasound signal, and the measuring the first shear wave parameter may include measuring the first shear wave parameter by applying a cross-correlation to the received plurality of first reflection signals.

The obtaining the elastic feature of the object may further include generating an image of an elasticity of the object by mapping the elastic feature to at least one from among a black and white scale and a color scale.

The transmitting the tracking ultrasound signal may include transmitting the first tracking ultrasound signal to a first position where the first shear wave has propagated and transmitting a second tracking ultrasound signal to a second position where the first shear wave has propagated, and the receiving the first reflection signal may include receiving the first reflection signal which relates to the first tracking ultrasound signal from the first position and receiving a second reflection signal which relates to the second tracking ultrasound signal from the second position. The measuring the first shear wave parameter may include measuring a first phase of the first shear wave from the first reflection signal and measuring a second phase of the first shear wave from the second reflection signal, and measuring a propagation velocity of the first shear wave by using a phase difference between the measured first phase and the measured second phase and by using a distance between the first position and the second position.

According to one or more exemplary embodiments, a method for obtaining an elastic feature of an object includes inducing a first sub-shear wave in the object by transmitting a first push ultrasound signal which is generated by a probe of an ultrasound apparatus, and inducing a second sub-shear wave in the object by transmitting a first grating lobe signal which relates to the first push ultrasound signal toward the object, transmitting a first tracking ultrasound signal to an area of the object where the first and second sub-shear waves have propagated, and receiving, from the object, a first reflection signal which relates to the first tracking ultrasound signal, measuring a first shear wave parameter of the first sub-shear wave and a second shear wave parameter of the second sub-shear wave based on the received first reflection signal, and using the measured first shear wave parameter of the first sub-shear wave and the measured second shear wave parameter of the second sub-shear wave to determine an average parameter value, and obtaining an elastic feature of the object by using the determined average parameter value.

The first push ultrasound signal may include an unfocused ultrasound signal.

The measuring the first shear wave parameter of the first sub-shear wave and the second shear wave parameter of the second sub-shear wave may include blocking a first component portion of the first reflection signal which relates to the first sub-shear wave by applying a first directional filter to the first reflection signal, and blocking a second component portion of the first reflection signal which relates to the second sub-shear wave by applying a second directional filter to the first reflection signal, and measuring the first shear wave parameter of the first sub-shear wave based on a result of the blocking the second component portion of the first reflection signal, and measuring the second shear wave parameter of the second sub-shear wave based on a result of the blocking the first component portion of the first reflection signal.

According to one or more exemplary embodiments, a non-transitory computer readable storage medium having stored thereon a program which, when executed by a computer, performs the method of obtaining an elastic feature of an object includes inducing a first shear wave in the object by transmitting a first push ultrasound signal which is generated by a probe of an ultrasound apparatus and a first grating lobe signal which relates to the first push ultrasound signal toward the object, transmitting a first tracking ultrasound signal to an area of the object where the first shear wave has propagated, and receiving, from the object, a first reflection signal which relates to the first tracking ultrasound signal, measuring a first shear wave parameter which indicates a shear wave characteristic of the first shear wave based on the first reflection signal, and obtaining an elastic feature of the object by using the first shear wave parameter.

According to one or more exemplary embodiments, a non-transitory computer readable storage medium having stored thereon a program which, when executed by a computer, performs the method of obtaining an elastic feature of an object includes inducing a first sub-shear wave in the object by transmitting a first push ultrasound signal which is generated by a probe of an ultrasound apparatus and inducing a second sub-shear wave in the object by transmitting a first grating lobe signal which relates to the first push ultrasound signal toward the object, transmitting a first tracking ultrasound signal to an area of the object where the first and second sub-shear waves have propagated, and receiving, from the object, a first reflection signal which relates to the first tracking ultrasound signal, measuring a first shear wave parameter of the first sub-shear wave and a second shear wave parameter of the second sub-shear wave based on the received first reflection signal, and using the measured first shear wave parameter of the first sub-shear wave and the measured second shear wave parameter of the second sub-shear wave to determine an average parameter value, and obtaining an elastic feature of the object by using the determined average parameter value.

According to one or more exemplary embodiments, an ultrasound apparatus may include a shear wave inducer configured to induce a first shear wave in an object by transmitting a first push ultrasound signal which is generated by a probe of the ultrasound apparatus and a first grating lobe signal which relates to the first push ultrasound signal toward the object, a shear wave detector configured to transmit a first tracking ultrasound signal to an area of the object where the first shear wave has propagated and to receive a first reflection signal which relates to the first tracking ultrasound signal from the object, and a controller configured to measure a first shear wave parameter which indicates a shear wave characteristic of the first shear wave based on the received first reflection signal and to obtain an elastic feature of the object by using the measured first shear wave parameter.

According to one or more exemplary embodiments, an ultrasound apparatus includes a shear wave inducer configured to induce a first sub-shear wave in an object by transmitting a first push ultrasound signal which is generated by a probe of an ultrasound apparatus and to induce a second sub-shear wave in the object by transmitting a first grating lobe signal which relates to the first push ultrasound signal toward the object, a shear wave detector configured to transmit a first tracking ultrasound signal to an area of the object where the first and second sub-shear waves have propagated, and to receive, from the object, a first reflection signal which relates to the first tracking ultrasound signal, and a controller configured to measure a first shear wave parameter of the first sub-shear wave and to measure a second shear wave parameter of the second sub-shear wave based on the received first reflection signal, to use the measured first shear wave parameter of the first sub-shear wave and the measured second shear wave parameter of the second sub-shear wave to determine an average parameter value, and to obtain an elastic feature of the object by using the determined average parameter value.

MODE FOR THE INVENTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

The terms such as "~portion", "~unit", "~module", and "~block" stated in the specification may signify a unit which is configured to process at least one function or operation, and the unit may be embodied by hardware such as a field-programmable gate array (FPGA) or an application-specific integrated circuit (ASIC), software, or a combination of hardware and software. However, the unit may be configured to be located in a storage medium to be addressed or configured to be able to operate one or more processors. Accordingly, the unit as an example includes constituent elements such as software constituent elements, object-oriented software constituent elements, class constituent elements, and task constituent elements, processes, functions, attributes, procedures, sub-routines, segments of program codes, drivers, firmware, microcodes, circuits, data, a database, data structures, tables, arrays, and variables. The constituent elements and functions provided by the "units" may be combined into a smaller number of constituent elements and units or may be further divided into additional constituent elements and units. Accordingly, the present exemplary embodiments are not limited by a specific combination of hardware and software.

In the present specification, an "image" may signify multi-dimensional data which is formed of discrete image elements, for example, pixels in a two-dimensional (2D) image and/or voxels in a three-dimensional (3D) image. For example, an image may include any one or more of an X-ray, a computed tomography (CT) image, a magnetic resonance imaging (MRI) image, an ultrasound image, and a medical image of an object which is acquired by other medical imaging apparatuses.

Further, in the present specification, an "object" may include any one or more of a human, an animal, or a part of a human or an animal. For example, an object may include organs such as the liver, the heart, the womb, the brain, a breast, the abdomen, etc., and/or blood vessels. In addition, an object may include a phantom that signifies matter which has a volume that approximates the intensity and effective atomic number of a living thing, and may include a sphere phantom which has a property similar to that of a human body.

Still further, in the present specification, a "user" may be a doctor, a nurse, a clinical pathologist, a medical imaging expert, a technician who fixes a medical apparatus, and/or any other suitable type of user, but the exemplary embodiments are not limited thereto.

FIG. 1 illustrates an ultrasound apparatus 100 which is configured for transmitting a first push ultrasound signal 113 and a first grating lobe signal 115 to an object 10, according to an exemplary embodiment. Referring to FIG. 1, the ultrasound apparatus 100 may include a probe 110 that transmits an ultrasound signal toward the object 10 and receives a reflection signal which is reflected from the object 10. The ultrasound apparatus 100 may generate an image of the object 10 by using the received reflection signal. The probe 110 may include an array probe which includes a plurality of elements 111 that are separately and/or independently controllable by the ultrasound apparatus 100.

The ultrasound apparatus 100, according to the present exemplary embodiment, transmits the first push ultrasound signal 113 and the first grating lobe signal 115 that is generated to correspond to the first push ultrasound signal 113 toward the object 10 via the probe 110 in order to induce a first shear wave which is generated by the first push ultrasound signal 113 and the first grating lobe signal 115 in the object 10.

The first grating lobe signal 115 is a signal which propagates in a non-axial direction and which is generated by the probe 110. In general, a grating lobe signal is a signal that should be removed because it reduces a lateral direction contrast aspect of an ultrasound image. The grating lobe signal may be weakened by reducing the width of an element of the probe 110 by an amount that makes the element width less than or equal to ½ of the wavelength of an ultrasound signal.

In the present exemplary embodiment, however, by designing the probe 110 such that the strength of the grating lobe signal equals the strength of a main beam, rather than weakening or removing the grating lobe signal generated by the probe 110, an induced shear wave in the object 10 may result from the transmission of the grating lobe signal.

The first push ultrasound signal 113 may include an unfocused ultrasound signal. The ultrasound apparatus 100, according to the present exemplary embodiment, transmits the first push ultrasound signal 113 toward the object 10 so that a risk due to a high sound pressure may be reduced.

Further, the ultrasound apparatus 100, according to the present exemplary embodiment, may transmit the first push ultrasound signal 113 toward the object 10 by steering the first push ultrasound signal 113 at a first steering angle "a". The steering angle signifies an angle between a preset reference axis 117 and a direction in which an ultrasound signal propagates. For example, the ultrasound apparatus 100 may set the first steering angle "a" of the first push ultrasound signal 113 to be within a range of between 0° and 90°. Accordingly, a shear wave may be induced in an area of the object 10 that is perpendicular to a position where the probe 110 is located.

In addition, the ultrasound apparatus 100, according to the present exemplary embodiment, may generate the first grating lobe signal 115 such that a steering angle "b" of the first grating lobe signal 115 is different from the first steering angle "a" of the first push ultrasound signal 113 by a predetermined angle. For example, the steering angle "b" of the first grating lobe signal 115 may be set to an angle which is determined by subtracting an angular measure of the first steering angle "a" of the first push ultrasound signal 113 from 180°. Accordingly, the first push ultrasound signal 113 and the first grating lobe signal 115 may be transmitted toward the object 10 in the symmetrical directions with respect to a center of a vertical axis 118 of the probe 110. The steering angle "b" of the first grating lobe signal 115 may be controlled by adjusting the pitch and width of an element of the probe 110.

FIG. 2 is a flowchart which illustrates a method for obtaining an elastic feature of the object 10, according to an exemplary embodiment. Referring to FIG. 2, in operation S210, the ultrasound apparatus 100 transmits, toward the object 10, the first push ultrasound signal 113 which is generated by the probe 110 and the first grating lobe signal 115 which relates to the first push ultrasound signal 113. As described above, the first push ultrasound signal 113 may include an unfocused ultrasound signal. The ultrasound apparatus 100 may transmit the first push ultrasound signal 113 toward the object 10 by steering the first push ultrasound signal 113 by the first steering angle "a".

In operation S220, the ultrasound apparatus 100 induces in the object 10 a first shear wave which is generated by the first push ultrasound signal 113 and the first grating lobe signal 115. The first shear wave which is induced in the object 10 will be described below with reference to FIG. 3.

In operation S230, the ultrasound apparatus 100 transmits a first tracking ultrasound signal to an area of the object 10 where the first shear wave has propagated.

In operation S240, the ultrasound apparatus 100 receives a first reflection signal from the object 10 which relates to the first tracking ultrasound signal.

In operation S250, the ultrasound apparatus 100 measures a first shear wave parameter which indicates a shear wave characteristic of the first shear wave, based on the first reflection signal which is received from the object 10. The first shear wave parameter may include at least one from among a propagation velocity of the first shear wave and an attenuation coefficient of the first shear wave.

The propagation velocity Vs of the first shear wave may be obtained by applying Equation 1, and the attenuation coefficient α of the first shear wave may be obtained by applying Equation 2. In Equations 1 and 2, "R" and "X" respectively are a real number component and an imaginary number of an acoustic impedance of the object 10, ρ is a density of the object 10, and ω is an angular frequency of the first shear wave.

$$V_s = \frac{R^2 + X^2}{\rho R} \quad \text{[Equation 1]}$$

$$\alpha = \frac{\rho \omega X}{(R^2 + X^2)} \quad \text{[Equation 2]}$$

Further, the ultrasound apparatus 100, according to the present exemplary embodiment, may measure the first shear wave parameter by transmitting the first tracking ultrasound signal multiple times toward the area where the first shear wave has propagated, receiving, from the object 10, a corresponding plurality of first reflection signals which respectively relate to the plurality of transmissions of the first tracking ultrasound signal toward the object 10, and then applying a cross-correlation to the plurality of received first reflection signals.

In addition to the above-described methods, the first shear wave parameter of the first shear wave which is induced in the object 10 may be measured by any one or more of a variety of methods within a scope that is well-known to those of ordinary skill in the art.

In operation S260, the ultrasound apparatus 100 may obtain an elastic feature of the object 10 by using the first shear wave parameter. The elastic feature of the object 10 may include at least one from among a shear modulus, a Young's modulus, and a shear viscosity of the object 10. A shear modulus G of the object 10 may be obtained by applying Equation 3. Young's modulus E of the object 10 may be obtained by applying Equation 4. A shear viscosity η of the object 10 may be obtained by applying Equation 5.

$$G = \frac{(R^2 - X^2)}{\rho} \quad \text{[Equation 3]}$$

$$E = 3G \quad \text{[Equation 4]}$$

$$\eta = \frac{2RX}{\omega \rho} \quad \text{[Equation 5]}$$

The ultrasound apparatus 100, according to the present exemplary embodiment, may generate an image of an elasticity of the object 10 by mapping the elastic feature of the object 10 to either or both of a black and white scale and a color scale, and output a generated image of the elasticity via a display (not shown).

FIG. 3 illustrates an exemplary method by which the ultrasound apparatus 100 induces a first shear wave in the object 10, according to an exemplary embodiment. Referring to FIG. 3, a first sub-shear wave 114 which is induced in the object 10 by the first push ultrasound signal 113 propagates in a direction A that is perpendicular to the direction in which the first push ultrasound signal 113 propagates. In addition, a second sub-shear wave 116 which is induced in the object 10 by the first grating lobe signal 115 propagates in a direction B that is perpendicular to the direction in which the first grating lobe signal 115 propagates.

When the steering angle of the first grating lobe signal 115 is set to be an angle which is determined by subtracting an angular measure of the steering angle of the first push ultrasound signal 113 from 180°, x-axis components of the first sub-shear wave 114 induced by the first push ultrasound signal 113 and the second sub-shear wave 116 induced by the first grating lobe signal 115 are offset with each other, and only y-axis components thereof remain. As a result, in an area where both the first and second sub-shear waves 114 and 116 exist, the first and second sub-shear waves 114 and 116 are synthesized with each other, and thus, the synthesized first shear wave exists and propagates in a direction C. The ultrasound apparatus 100, according to the present exemplary embodiment, may obtain an elastic feature of the object 10 by measuring the first shear wave parameter of the first shear wave that propagates in the direction C.

FIG. 4 illustrates an exemplary method by which the ultrasound apparatus 100 induces a first shear wave in the object 10, according to another exemplary embodiment. Referring to FIG. 4, the ultrasound apparatus 100, according to the present exemplary embodiment, may transmit a plurality of first push ultrasound signals 113 and a corresponding plurality of first grating lobe signals 115 which respectively relate to the first push ultrasound signals 113, both pluralities having a same steering angle, by using a plurality of elements 111, thereby inducing in the object 10 a first shear wave that is generated by the first push ultrasound signals 113 and the first grating lobe signals 115.

When a first shear wave is induced in the object 10 by using only one first push ultrasound signal 113 and one first grating lobe signal 115, the strength of the first shear wave may be weak, and therefore, in the present exemplary embodiment, the first shear wave is induced in the object 10 by using at least two of the first push ultrasound signals 113 and at least two of the first grating lobe signals 115. IN order to enable the first sub-shear waves 114 induced by the first push ultrasound signals 113 to overlap with each other, an interval between the first push ultrasound signals 113 is adjusted.

FIG. 5 is a flowchart which illustrates a method for obtaining an elastic feature of the object 10, according to another exemplary embodiment. The method for obtaining an elastic feature of the object 10 which is illustrated in FIG. 5 may be performed instead of operation S260 of FIG. 2.

In operation S510, the ultrasound apparatus 100 transmits, to the object 10, a second push ultrasound signal that is steered at a second steering angle which is different from the first steering angle of the first push ultrasound signal 113, and also transmits a second grating lobe signal which corresponds to the second push ultrasound signal.

In operation S520, the ultrasound apparatus 100 induces, in the object 10, a second shear wave that is generated by the second push ultrasound signal and the second grating lobe signal.

In operation S530, the ultrasound apparatus 100 transmits a second tracking ultrasound signal to an area of the object 10 where the second shear wave has propagated.

In operation S540, the ultrasound apparatus 100 receives a second reflection signal which relates to the second tracking ultrasound signal from the object 10.

In operation S550, the ultrasound apparatus 100 measures a second shear wave parameter which indicates a shear wave characteristic of the second shear wave, based on the received second reflection signal. The method for measuring the shear wave parameter based on the reflection signal has already been described above with reference to FIG. 2, and thus, a detailed description thereof will be omitted here.

In operation S560, the ultrasound apparatus 100 determines an average parameter value of the first shear wave parameter measured in operation S250 of FIG. 2 and the second shear wave parameter. The ultrasound apparatus 100 may determine the average parameter value of the first and second shear wave parameters by applying a respective weight to each of the first and second shear wave parameters.

In operation S570, the ultrasound apparatus 100 obtains an elastic feature of the object 10 by using the determined average parameter value.

According to a method for obtaining an elastic feature of the object 10 according to another exemplary embodiment, because the elastic feature of the object 10 is obtained after determining an average parameter value of the first shear wave parameter of the first shear wave which is induced by the first push ultrasound signal 113 and the first grating lobe signal 115 and the second shear wave parameter of the second shear wave which is induced by the second push ultrasound signal and the second grating lobe signal, the elastic feature of the object 10 may be relatively more accurately obtained.

FIG. 6 illustrates a method by which the ultrasound apparatus 100 measures a propagation velocity of the first shear wave, according to an exemplary embodiment. Reference will be made to FIG. 6 to describe an exemplary method other than the above-described method for measuring the first shear wave parameter of the first shear wave in FIG. 2.

The ultrasound apparatus 100, according to the present exemplary embodiment, may transmit a first tracking ultrasound signal 610 to a first position 601 in an area where the first shear wave has propagated, and receive a first reflection signal which is reflected from the first position 601. Next, the ultrasound apparatus 100 may transmit a second tracking ultrasound signal 630 to a second position 603 in an area where the first shear wave has propagated, and receive a second reflection signal which is reflected from the second position 603. The ultrasound apparatus 100 may measure a first phase of the first shear wave from the first reflection signal and a second phase of the first shear wave from the second reflection signal.

In detail, the ultrasound apparatus 100 measures a first phase of the first shear wave that passes through the first position 601 by using the first reflection signal, and measures a second phase of the first shear wave that passes through the second position 603 by using the second reflection signal. The ultrasound apparatus 100 may measure a propagation velocity of the first shear wave as the first shear wave parameter by using a phase difference between the measured first and second phases and a distance d between the first and second positions 601 and 603.

For example, the ultrasound apparatus 100 may obtain a propagation velocity Cs of the first shear wave by applying Equation 6. In Equation 6, $\omega$ is an angular frequency of the first shear wave, $\Delta r$ is a distance d between the first and second positions, and $\Delta \varphi$ is a phase difference between the first and second phases.

$$c_s = \frac{\omega \Delta r}{\Delta \phi} \quad \text{[Equation 6]}$$

Although in the above description the first shear wave parameter of the first shear wave induced in the object 10 is measured, it is possible to obtain an elastic feature of the object 10 by measuring a first shear wave parameter of the first sub-shear wave 114 which is induced in the object 10 by the first push ultrasound signal 113 and by measuring a second shear wave parameter of the second sub-shear wave 116 which is induced in the object 10 by the first grating lobe signal 115 and using the measured first and second shear wave parameters.

FIG. 7 is a flowchart which illustrates a method for obtaining an elastic feature of the object 10, according to another exemplary embodiment.

In operation S710, the ultrasound apparatus 100 transmits, to the object 10, the first push ultrasound signal 113 which is generated by the probe 110 of the ultrasound apparatus 100 and the corresponding first grating lobe signal 115 which relates to the first push ultrasound signal 113. In operation S720, the ultrasound apparatus 100 induces, in the object 10, the first sub-shear wave 114 which is generated by the first push ultrasound signal 113 and the second sub-shear wave 116 which is generated by the first grating lobe signal 115. In operation S730, the ultrasound apparatus 100 transmits a first tracking ultrasound signal to an area of the ultrasound apparatus 100 where the first sub-shear wave 114 and the second sub-shear wave 116 have propagated. In operation S740, the ultrasound apparatus 100 receives, from the object 10, a first reflection signal which relates to the first tracking ultrasound signal.

In operation S750, the ultrasound apparatus 100 measures a first shear wave parameter of the first sub-shear wave 114 and a second shear wave parameter of the second sub-shear wave 116 based on the received first reflection signal. Because the first and second sub-shear waves 114 and 116 may be offset in the object 10, the ultrasound apparatus 100 may measure the respective first and second shear wave parameters of the first and second sub-shear waves 114 and 116 by applying the first reflection signal to a directional filter and using a filtered reflection signal.

For example, the ultrasound apparatus 100 may block a first component portion of the first reflection signal, which first component portion corresponds to the first sub-shear wave 114, by applying a first directional filter to the first reflection signal which is received from the object 10, and may block a second component portion of the first reflection signal, which second component portion corresponds to the second sub-shear wave 116, by applying a second directional filter to the first reflection signal. Next, the ultrasound apparatus 100 may measure the first shear wave parameter of the first sub-shear wave 114 based on a result of the blocking the second component portion of the first reflection signal, and may measure the second shear wave parameter of the second sub-shear wave 116 based on a result of the blocking the first component portion of the first reflection signal. Because the directional filter is well-known to those of ordinary skill in the art, a detailed description thereof will be omitted herein.

In operation S760, the ultrasound apparatus 100 determines an average parameter value of the first shear wave parameter of the first sub-shear wave 114 and the second shear wave parameter of the second sub-shear wave 116. The ultrasound apparatus 100 may apply a respective weight to each of the first shear wave parameter of the first sub-shear wave 114 and the second shear wave parameter of the second sub-shear wave 116, and then may determine an average value of the first shear wave parameter of the first sub-shear wave 114 to which a first weight is applied and the second shear wave parameter of the second sub-shear wave 116 to which a second weight is applied.

In operation S770, the ultrasound apparatus 100 may obtain an elastic feature of the object 10 by using the average parameter value which is determined in operation S760.

According to a method for obtaining an elastic feature of the object 10 according to another exemplary embodiment, the ultrasound apparatus 100 may measure the first shear wave parameter of the first sub-shear wave 114 and the second shear wave parameter of the second sub-shear wave 116 by one-time scanning, and then accurately and quickly obtain an elastic feature of the object 10 by using a result of the measurements.

FIG. 8 is a block diagram which illustrates a structure of an ultrasound apparatus 800, according to an exemplary embodiment. Referring to FIG. 8, the ultrasound apparatus 800 may include a shear wave induction unit (also referred to herein as a "shear wave inducer") 810, a shear wave detection unit (also referred to herein as a "shear wave detector") 830, and a control unit (also referred to herein as a "controller") 850. Each of the shear wave induction unit 810, the shear wave detection unit 830, and the control unit 850 may be configured by using a microprocessor.

The shear wave induction unit 810 controls the probe 110 to transmit the first push ultrasound signal 113 which is generated by the probe 110 and the corresponding first grating lobe signal 115 which relates to the first push ultrasound signal 113 toward the object 10, thereby inducing in the object 10 a first shear wave that is generated by the first push ultrasound signal 113 and the first grating lobe signal 115. The first push ultrasound signal 113 may include an unfocused ultrasound signal and may have a steering angle which falls within a range of between 0° and 90°. The first shear wave may include a shear wave which is obtained by synthesizing a first sub-shear wave 114 which is generated by the first push ultrasound signal 113 and a second sub-shear wave 116 which is generated by the first grating lobe signal 115.

The shear wave induction unit 810 may transmit a plurality of first push ultrasound signals 113 and a corresponding plurality of first grating lobe signals 115 which respectively relate to the first push ultrasound signals 113, both pluralities having a same steering angle, toward the object by using a plurality of elements 111 which are included in the probe 110 of the ultrasound apparatus 800, thereby inducing in the object 10 the first shear wave that is generated by the first push ultrasound signals 113 and the first grating lobe signals 115.

The shear wave induction unit 810 may transmit, toward the object 10, a second push ultrasound signal which has a second steering angle which is different from a first steering angle of the first push ultrasound signal 113, and a corresponding second grating lobe signal which relates to the second push ultrasound signal, thereby inducing in the object 10 a second shear wave which is generated by the second push ultrasound signal and the second grating lobe signal.

The shear wave detection unit 830 controls the probe 110 to transmit a first tracking ultrasound signal to an area of the object 10 where at least one of the first shear wave and the second shear wave has propagated, and to receive, from the object 10, a first reflection signal which relates to the first tracking ultrasound signal.

The shear wave detection unit 830 may transmit the first tracking ultrasound signal a plurality of times to the area of the object 10 where at least one of the first shear wave and the second shear wave has propagated, and receive, from the object 10, a corresponding plurality of first reflection signals which respectively relate to the plurality of transmissions of first tracking ultrasound signals to the object 10.

The control unit 850 may measure a first shear wave parameter which indicates a shear wave characteristic of the first shear wave based on the first reflection signal which is received by the probe 110, and obtain an elastic feature of the object 10 by using the measured first shear wave parameter.

Further, the control unit 850 may measure a first shear wave parameter of the first sub-shear wave 114 and a second shear wave parameter of the second sub-shear wave 116 based on the first reflection signal which is received by the probe 110, determine an average parameter value by using the measured first shear wave parameter of the first sub-shear wave 114 and the measured second shear wave parameter of the second sub-shear wave 116, and obtain the elastic feature of the object 10 by using the determined average. The control unit 850 may apply a first directional filter and a second directional filter to the first reflection signal which is received by the probe 110 in order to measure an accurate respective value of each of the first shear wave parameter of the first sub-shear wave 114 and the second shear wave parameter of the second sub-shear wave 116.

In addition, when the shear wave detection unit 830 receives the first reflection signal from the area of the object 10 where the second sub-shear wave has propagated, the control unit 850 may measure the second shear wave parameter which indicates the shear wave characteristic of the second sub-shear wave, determine an average parameter value of the first and second shear wave parameters, and obtain the elastic feature of the object 10 by using the determined average parameter value.

Although it is not illustrated in FIG. 8, the ultrasound apparatus 800, according to the present exemplary embodiment, may further include an image generation unit (also referred to herein as an "image generator") which is configured for generating an image of an elasticity of the object 10 by mapping the elastic feature of the object 10 to at least one from among a black and white scale and a color scale, and a display which is configured for outputting a generated image of elasticity of the object 10.

The display may include any one or more of a cathode-ray tube (CRT) display, a liquid-crystal display (LCD) display, a plasma display panel (PDP) display, an organic light-emitting diode (OLED) display, a field emission display (FED) display, a light-emitting diode (LED) display, a vacuum fluorescent display (VFD) display, a digital light processing (DLP) display, a primary flight display (PFD) display, a 3D display, a transparent display, and/or any other suitable type of display, and a variety of display apparatuses within a range that is well-known to those of ordinary skill in the art.

In addition, other exemplary embodiments can also be implemented via computer readable code/instructions which are stored in/on a medium, e.g., a computer readable medium, in order to control at least one processing element to implement any of the above described exemplary embodiments. The medium can correspond to any transitory or non-transitory medium/media which permits the storage and/or transmission of the computer readable code.

The computer readable code can be recorded/transferred on a medium in any one or more of a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present inventive concept as defined by the following claims.

The invention claimed is:

1. A method for obtaining an elastic feature of an object, the method comprising:
   inducing a first shear wave in the object by transmitting a first push ultrasound signal which is generated by a probe of an ultrasound apparatus and a first grating lobe signal which relates to the first push ultrasound signal toward the object;
   transmitting a first tracking ultrasound signal to an area of the object where the first shear wave has propagated, and receiving, from the object, a first reflection signal which relates to the first tracking ultrasound signal;
   measuring a first shear wave parameter which indicates a shear wave characteristic of the first shear wave based on the first reflection signal; and
   obtaining an elastic feature of the object by using the measured first shear wave parameter,
   wherein the first push ultrasound signal induces a first sub-shear wave propagating in a first direction and the first grating lobe signal induces a second sub-shear wave propagating in a second direction different from the first direction, and
   wherein the first shear wave is a synthesis of the first sub-shear wave and the second sub-shear wave.

2. The method of claim 1, wherein the first push ultrasound signal comprises an unfocused ultrasound signal.

3. The method of claim 1, wherein the first shear wave is induced in the object by transmitting a plurality of first push ultrasound signals and a plurality of first grating lobe signals which respectively relate to the plurality of first push ultrasound signals, both pluralities having a same steering angle, toward the object by using a plurality of elements which are included in the probe, and
   wherein the plurality of first push ultrasound signals comprises the first path ultrasound signal and the plurality of first grating lobe signals comprises the first grating lobe signal.

4. The method of claim 1, wherein the inducing the first shear wave comprises transmitting the first push ultrasound signal toward the object by steering the first push ultrasound signal at a first steering angle.

5. The method of claim 4, further comprising:
   inducing a second shear wave in the object by transmitting a second push ultrasound signal which is steered at a second steering angle that is different from the first steering angle and a second grating lobe signal which relates to the second push ultrasound signal toward the object;
   transmitting a second tracking ultrasound signal to an area of the object where the second shear wave has propagated and receiving, from the object, a second reflection signal which relates to the second tracking ultrasound signal; and
   measuring a second shear wave parameter which indicates a shear wave characteristic of the second shear wave based on the second reflection signal,
   wherein the obtaining the elastic feature of the object comprises using the measured first shear wave parameter and the measured second shear wave parameter to determine an average parameter value and obtaining the elastic feature of the object by using the determined average parameter value.

6. The method of claim 1, wherein the receiving the first reflection signal comprises transmitting the first tracking ultrasound signal a plurality of times to an area where the first shear wave has propagated and receiving, from the object, a plurality of first reflection signals which relate to the plurality of transmissions of the first tracking ultrasound signal, and the measuring the first shear wave parameter comprises measuring the first shear wave parameter by applying a cross-correlation to the received plurality of first reflection signals.

7. The method of claim 1, wherein the obtaining the elastic feature of the object further comprises generating an image of an elasticity of the object by mapping the elastic feature to at least one from among a black and white scale and a color scale.

8. The method of claim 1, wherein the transmitting the first tracking ultrasound signal comprises:

transmitting the first tracking ultrasound signal to a first position where the first shear wave has propagated and transmitting a second tracking ultrasound signal to a second position where the first shear wave has propagated, wherein the receiving the first reflection signal comprises:

receiving the first reflection signal which relates to the first tracking ultrasound signal from the first position and receiving a second reflection signal which relates to the second tracking ultrasound signal from the second position, and wherein the measuring the first shear wave parameter comprises:

measuring a first phase of the first shear wave from the first reflection signal and measuring a second phase of the first shear wave from the second reflection signal; and measuring a propagation velocity of the first shear wave by using a phase difference between the measured first phase and the measured second phase and by using a distance between the first position and the second position.

9. A non-transitory computer readable storage medium having stored thereon a program which, when executed by a computer, causes the computer and the probe of the ultrasound apparatus to perform the method of claim 1.

10. The method of claim 1, wherein a component of the first sub-shear wave that is perpendicular to a vertical axis of the probe offsets a component of the second sub-shear wave that is perpendicular to the vertical axis of the probe.

11. The method of claim 1, wherein the first shear wave propagates in a direction parallel to a vertical axis of the probe.

12. The method of claim 10, wherein the first shear wave propagates in a direction parallel to a vertical axis of the probe.

13. An ultrasound apparatus comprising:

a shear wave inducer configured to induce a first shear wave in an object by transmitting a first push ultrasound signal which is generated by a probe of the ultrasound apparatus and a first grating lobe signal which relates to the first push ultrasound signal toward the object;

a shear wave detector configured to transmit a first tracking ultrasound signal to an area of the object where the first shear wave has propagated and to receive a first reflection signal which relates to the first tracking ultrasound signal from the object; and a controller configured to measure a first shear wave parameter which indicates a shear wave characteristic of the first shear wave based on the received first reflection signal and to obtain an elastic feature of the object by using the measured first shear wave parameter, wherein the first push ultrasound signal induces a first sub-shear wave propagating in a first direction and the first grating lobe signal induces a second sub-shear wave propagating in a second direction different from the first direction, and wherein the first shear wave is a synthesis of the first sub-shear wave and the second sub-shear wave.

* * * * *